(12) United States Patent
Mitchell et al.

(10) Patent No.: US 8,409,637 B2
(45) Date of Patent: Apr. 2, 2013

(54) COMPOSITIONS AND METHODS FOR TREATING AND PREVENTING MIGRAINOUS HEADACHES AND ASSOCIATED SYMPTOMS

(75) Inventors: Russell W Mitchell, Schofield, WI (US); James W. Higgins, Schofield, WI (US)

(73) Assignee: Puramed Bioscience Inc., Schofield, WI (US)

( * ) Notice: Subject to any disclaimer, the term of this patent is extended or adjusted under 35 U.S.C. 154(b) by 0 days.

(21) Appl. No.: 12/144,391

(22) Filed: Jun. 23, 2008

(65) Prior Publication Data

US 2008/0317887 A1 Dec. 25, 2008

Related U.S. Application Data

(60) Provisional application No. 60/945,502, filed on Jun. 21, 2007.

(51) Int. Cl.
*A61K 36/28* (2006.01)
*A61K 36/906* (2006.01)

(52) U.S. Cl. .................... 424/756; 424/764

(58) Field of Classification Search .............. None
See application file for complete search history.

(56) References Cited

U.S. PATENT DOCUMENTS

| | | | |
|---|---|---|---|
| 4,758,433 A | 7/1988 | Johnson et al. | |
| 5,384,121 A | 1/1995 | Rhodes | |
| 5,466,451 A | 11/1995 | Beuscher et al. | |
| 6,312,736 B1 | 11/2001 | Kelly et al. | |
| 6,328,715 B1 | 12/2001 | Dragan et al. | |
| 7,192,614 B2 * | 3/2007 | Mitchell et al. | 424/756 |
| 2004/0086579 A1 * | 5/2004 | Higgins et al. | 424/729 |
| 2004/0086582 A1 * | 5/2004 | Mitchell et al. | 424/756 |
| 2004/0247705 A1 * | 12/2004 | Roberts | 424/729 |
| 2005/0186269 A1 * | 8/2005 | Udell et al. | 424/458 |
| 2006/0013904 A1 * | 1/2006 | Roberts et al. | 424/756 |
| 2006/0222722 A1 * | 10/2006 | Roberts et al. | 424/756 |

FOREIGN PATENT DOCUMENTS

| | | |
|---|---|---|
| GB | 2 166 952 A | 5/1986 |
| WO | 92/11857 A1 | 7/1992 |
| WO | 94/06800 A1 | 3/1994 |
| WO | 98/39018 A1 | 9/1998 |
| WO | 2004/110468 A1 | 12/2004 |

OTHER PUBLICATIONS

"Chemical Characteristics" www.oliveoilsource.com/page/chemical-characteristics.*
"Prevalence of Migraine Headache in the United States," Stewart et al, JAMA, Jan. 1, 1992—vol. 267, No. 1: 64-69.
"Migraine Diagnosis and Treatment: Results from the American Migraine Study II," Lipton et al, Headache 2001; 41: 638-645.
"Assessment of health-related quality of life in migraine," Dahlof, Cephalalgia 1993; 13:233-237.
"Assessing and Understanding Patient Risk," Fries, Scand J. Rheumatol 1992; Suppl; 92: 21-24.
PDR for Herbal Medicines, Thompson Medical Economics, Second Edition, Feverfew: 306, 309 and Ginger, 339 342, 2000.
"Randomised Double-Blind Placebo-Controlled Trial of Feverfew in Migraine Prevention," Murphy et al., The Lancet, Jul. 23, 1988; 2; 189-192.
"Efficacy of feverfew as prophylactic treatment of migraine," Johnson et al., British Medical Journal, Aug. 31, 1985; vol. 291:569-573.

* cited by examiner

*Primary Examiner* — Christopher R. Tate
*Assistant Examiner* — Deborah A. Davis
(74) *Attorney, Agent, or Firm* — Akerman Senterfitt

(57) ABSTRACT

Compositions and methods of treating migrainous headaches and their associated symptoms are provided. Methods of treating migrainous headaches and their associated symptoms include administering a lipid-based composition containing feverfew extract and ginger extract sublingually to a patient in need thereof. Treatments are effective using low total administered amounts of feverfew and ginger extracts.

8 Claims, 4 Drawing Sheets

| NF-kB p65 ACTIVITY | 8/30/2007 | 9/3/2007 | | | | | % OF |
|---|---|---|---|---|---|---|---|
| SAMPLE | RLU (EXPT. 1) | RLU (EXPT. 2) | MEAN RLU | SD | CV | -Bkgd | LPS |
| BLANK (UNTREATED CELLS) | 23343418 | 24781919 | 24062668 | 1017174 | 4 | 0 | 0 |
| F1 50 ug/ml | 18222267 | 26619773 | 22421020 | 5937934 | 26 | -1641648 | -7 |
| F1 100 ug/ml | 20251716 | 29848248 | 25049982 | 6785773 | 27 | 987314 | 4 |
| F2 50 ug/ml | 35009186 | 38038231 | 36523708 | 2141858 | 6 | 12461040 | 54 |
| F2 100 ug/ml | 36026287 | 36654599 | 36340443 | 444284 | 1 | 12277775 | 53 |
| F3 50 ug/ml | 15527425 | 22590004 | 19058714 | 4993998 | 26 | -5003954 | -22 |
| F3 100 ug/ml | 18174739 | 27579464 | 22877102 | 6650145 | 29 | -1185566 | -5 |
| RES 50 ug/ml | 21069199 | 30910430 | 25989815 | 6958801 | 27 | 1927147 | 8 |
| RES 100 ug/ml | 19572065 | 23572988 | 21572526 | 2829080 | 13 | -2490142 | -11 |
| CONTROL 50 ug/ml | 34709759 | 37973009 | 36341384 | 2307466 | 6 | 12278716 | 53 |
| CONTROL 100 ug/ml | 30969299 | 33794161 | 32381730 | 1997479 | 6 | 8319062 | 36 |
| F1 50 ug/ml +LPS 20 ng/ml | 28759243 | 33407490 | 31083366 | 3286807 | 11 | 7020698 | 31 |
| F1 100 ug/ml +LPS 20 ng/ml | 22195615 | 22520123 | 22357869 | 229462 | 1 | -1704799 | -7 |
| F2 50 ug/ml +LPS 20 ng/ml | 29006389 | 35531854 | 32269121 | 4614200 | 14 | 8206453 | 36 |
| F2 100 ug/ml +LPS 20 ng/ml | 28935097 | 30253554 | 29594326 | 932290 | 3 | 5531658 | 24 |
| F3 50 ug/ml +LPS 20 ng/ml | 29424636 | 29307839 | 29366238 | 82588 | 0 | 5303570 | 23 |
| F3 100 ug/ml +LPS 20 ng/ml | 23740277 | 25571567 | 24655922 | 1294918 | 5 | 593254 | 3 |
| RES 50 ug/ml +LPS 20 ng/ml | 44139331 | 53570314 | 48854822 | 6668712 | 14 | 24792154 | 108 |
| RES 100 ug/ml +LPS 20 ng/ml | 46775163 | 65344056 | 56059609 | 13130190 | 23 | 31996941 | 139 |
| RAW MATERIAL 50 ug/ml +LPS 20 ng/ml | 41434983 | 55540941 | 48487962 | 9974419 | 21 | 24425294 | 106 |
| RAW MATERIAL 100 ug/ml +LPS 20 ng/ml | 33412242 | 44481204 | 38946723 | 7826937 | 20 | 14884055 | 65 |
| LPS 20 ng/ml | 47528083 | 46586933 | 47057508 | 665494 | 1 | 22994840 | 100 |

FIG. 1

| SAMPLE | MEAN NITRATE (μM) | SD | -Bkgr | % OF LPS | MEAN NITRATE (μM) | SD | -Bkgr | % OF LPS |
|---|---|---|---|---|---|---|---|---|
| F1 50 μg/ml | 0.791 | 0.09 | 0.462 | 4 | 0.438 | 0.112 | -0.137 | -5 |
| F1 100 μg/ml | 0.666 | 0.086 | 0.337 | 3 | 0.463 | 0.147 | -0.112 | -4 |
| F2 50 μg/ml | 0.513 | 0.046 | 0.184 | 2 | 0.19 | 0.158 | -0.385 | -14 |
| F2 100 μg/ml | 0.655 | 0.282 | 0.326 | 3 | 0.927 | 0.164 | 0.352 | 12 |
| F3 50 μg/ml | 0.621 | 0.022 | 0.292 | 3 | 0.386 | 0.118 | -0.189 | -7 |
| F3 100 μg/ml | 0.762 | 0.307 | 0.433 | 4 | 0.585 | 0.319 | 0.01 | 0 |
| RES 50 μg/ml | 0.513 | 0.046 | 0.184 | 2 | 0.662 | 0.348 | 0.087 | 3 |
| RES 100 μg/ml | 0.808 | 0.243 | 0.479 | 4 | 0.963 | 0.613 | 0.388 | 14 |
| CONTROL 50 μg/ml | 0.887 | 0.483 | 0.558 | 5 | 0.805 | 0.146 | 0.23 | 8 |
| CONTROL 100 μg/ml | 0.762 | 0.307 | 0.433 | 4 | 1.35 | 0.273 | 0.775 | 27 |
| | | | | | | | | |
| F1 50+LPS 20 μg/ml | 0.978 | 0.354 | 0.649 | 6 | 0.589 | 0.245 | 0.014 | 0 |
| F1 100+LPS 20 μg/ml | 0.87 | 0.33 | 0.541 | 5 | 0.601 | 0.503 | 0.026 | 1 |
| F2 50+LPS 20 μg/ml | 0.932 | 0.419 | 0.603 | 6 | 1.098 | 0.406 | 0.523 | 18 |
| F2 100+LPS 20 μg/ml | 1.011 | 0.659 | 0.682 | 6 | 0.483 | 0.74 | -0.092 | -3 |
| F3 50 μg/ml+LPS 20 ng/ml | 0.7 | 0.218 | 0.371 | 3 | 0.528 | 0.4 | -0.047 | -2 |
| F3 100 μg/ml+LPS 20 ng/ml | 1.181 | 0.771 | 0.852 | 8 | 0.731 | 0.526 | 0.156 | 6 |
| RES 50 μg/ml+LPS 20 ng/ml | 6.629 | 3.46 | 6.3 | 58 | 3.296 | 1.25 | 2.721 | 96 |
| RES 100 μg/ml+LPS 20 ng/ml | 2.824 | 2.322 | 2.495 | 23 | 2.058 | 0.791 | 1.483 | 52 |
| CONTROL 50 μg/ml+LPS 20 ng/ml | 2.927 | 1.825 | 2.598 | 24 | 1.782 | 0.561 | 1.207 | 43 |
| CONTROL 100 μg/ml+LPS 20 ng/ml | 1.085 | 0.378 | 0.756 | 7 | 1.676 | 0.088 | 1.101 | 39 |
| LPS 20 ng/ml | 11.103 | 2.516 | 10.774 | 100 | 3.41 | 1.329 | 2.835 | 100 |
| BLANK | 0.329 | 0.199 | 0 | 0 | 0.575 | 0.042 | 0 | 0 |

FIG. 3

COMPOSITIONS AND METHODS FOR TREATING AND PREVENTING MIGRAINOUS HEADACHES AND ASSOCIATED SYMPTOMS

CROSS REFERENCE TO RELATED APPLICATION

The present application claims the priority of U.S. provisional patent application No. 60/945,502 filed Jun. 21, 2007.

FIELD OF THE INVENTION

The invention relates generally to the field of medicine. More particularly, the invention relates to compositions and methods for treating migrainous headaches and their associated symptoms.

BACKGROUND OF THE INVENTION

Headaches are a common complaint heard by primary care physicians and account for more than 10 million office visits each year in the United States (US). The American Migraine Study reports that 32 million Americans suffer from at least one migraine headache annually, and that 23 million people in the US suffer from "severe migraines" (Stewart W F JAMA 1992; 267:64 9, Lipton, R B Headache. 2001; 41:638 645). The cost of migraines and their associated symptoms to the US economy is greater than $14 billion per year.

A migraine is a severe headache that is usually recurrent and disabling. More than 85% of women and more than 82% of men with severe headache had some headache-related disability (Stewart W F, JAMA 1992; 267:64 9). Approximately 33% were severely disabled or needed bed rest during an attack. Many who suffer from migraines experience chronic anxiety, fearing the next attack and find their ability to work, to take care of their families, and to meet social obligations is disrupted. Disability, therefore, occurs not only during attacks but also between attacks. Quality of life measurements have shown that those who suffer from migraines, compared to those with other chronic illnesses, have lower scores in physical functioning and role functioning, and also experience more body pain (Dahlof, C Cephalalgia 1993; 13:233-237).

Migraine headaches can induce a number of serious physical conditions, including strokes, aneurysms, permanent visual loss, severe dental problems, coma and even death. Migraine and epileptic seizure disorders are also related, e.g., a migraine-triggered epilepsy. In addition to the physical conditions associated with the migraine headache itself, over-the-counter (OTC) products used by people who suffer from migraines, such as aspirin, acetaminophen, ibuprofen and other common analgesics, exhibit side effects associated with both chronic use and short-term overuse. These side effects are frequently severe and may include liver damage, kidney damage, ulcers and stomach upset. Each year, use of non-steroidal anti-inflammatory drugs such as aspirin and ibuprofen, account for an estimated 7600 deaths and 76000 hospitalizations in the US (Fries J F. Assessing and understanding patient risk. Scand J Rheumatol Suppl. 1992; 92:21 4.). Frequent use of OTC analgesics has been recognized as a substantial contributor to the development of daily headaches ("chronic daily headache"). Rebound headaches are also associated with the use of OrC analgesics, especially with products incorporating caffeine or aspirin.

The triptans are a class of medication frequently used to treat migraines including, for example, Imitrex, Zomig, and Maxalt. The side effects commonly observed with this class of drugs include chest pain, shortness of breath, palpitations, paresthesias, asthenia, dizziness, dry mouth, fatigue, hot flashes, nausea, vomiting, and sleepiness. Less common side effects include chills, constipation, diarrhea, heartburn, joint pain, central nervous system effects (agitation, anxiety, confusion, depression, irritability), eye problems (e.g., blurred vision, dry eyes, irritated eyes), dysphagia, euphoria, heat sensitivity, hypertension, flatulence, increased sweating, increased thirst, polyuria, pruritis, insomnia, muscle stiffness, muscle pain or spasms, tinnitus, tremor, vertigo, and warm or cold sensations.

A study by Lipton, R Headache Vol 41, pp 638 645, August 2001 revealed that more than half of all Americans who suffer from migraine headaches are prepared to put up with the pain rather than seek treatment from a physician, and that 26% had stopped seeing their doctor about the condition because they felt the doctor could not help. Commercially available migraine treatments are associated with a number of disadvantages, including side effects that are often severe. Thus, a treatment for migrainous headaches and the symptoms associated with migrainous headaches that is not only effective at treating but also at preventing migrainous headaches and associated symptoms without side effects would satisfy a great need.

SUMMARY OF THE INVENTION

The invention relates to the discovery that migrainous headaches and their associated symptoms may be treated by administration of a surprisingly small amount of parthenolide, and more preferably a small amount of feverfew extract, when said treatment is sublingually administered as a lipid-based composition for at least 60 seconds. Feverfew is an herb from the lianacetum parthenium plant and is rich in compounds known as sesquiterpene lactones. The most prevalent of these compounds is parthenolide. The concentration of feverfew in the compositions described herein is significantly less than the concentrations of feverfew found in currently available forms of feverfew, including fresh feverfew leaves which have been known to be chewed by people wishing to rid themselves of migraine headaches and commercially available feverfew products. Although manufacturers generally emphasize the benefits of larger doses of feverfew, the compositions as described herein contain feverfew extract at a smaller concentration of about 3 mg to about 60 mg in a two-hour period. Additionally, the feverfew-containing compositions of the invention are more palatable than fresh feverfew leaves, and do not result in undesirable side effects such as sores in the mouth and sensitization of oral tissues that have been reported by those who have chewed fresh feverfew leaves, for example. Another advantage of the compositions and methods of the invention is the use of lipids for forming the compositions. The use of lipids is advantageous because lipids are compatible with the oil-soluble actives that are included in the compositions and because lipids result in the compositions having greater stability over non-lipid-based compositions.

The compositions and methods described herein have been found to be effective both as an acute (abortive) treatment and as a preventative (prophylactic) treatment. The combination of the correct dosage of active ingredient, together with the correct route of administration for these compositions results in a surprising degree of effectiveness for patients in need of acute and/or preventative treatment of migrainous headaches.

Accordingly, the invention features a method of treating migrainous headaches. The method includes administering a lipid-based composition containing at least one lipid, feverfew extract and ginger extract sublingually to a patient in need thereof in a total administered amount of from about 3 mg to about 60 mg of feverfew extract in a two hour period. The total administered amount can be from about 3 mg to about 60 mg of feverfew extract in a two hour period. The feverfew extract can have a standardized parthenolide concentration of from about 0.7% to about 20%. The composition can further include a mucosal permeation enhancer. The total administered amount can be divided among a plurality of compositions that are administered sequentially. The composition can be held sublingually for at least about 60 seconds prior to swallowing, e.g., while being circulated about the mouth prior to swallowing.

Also included within the invention is a method of treating migrainous headaches. The method includes administering a lipid-based composition containing at least one lipid, feverfew extract and ginger extract sublingually to a patient in need thereof in a total administered amount of from about 3 mg to about 90 mg of feverfew extract in a 24 hour period. The feverfew extract can be administered in at least two doses, and each individual dose of feverfew extract may not exceed about 15 mg.

Also included within the invention is a composition for sublingual administration including: at least one lipid; feverfew extract at a concentration of about 3 to about 60 mg; and ginger extract at a concentration of about 0.1 to about 10% of the composition.

Unless otherwise defined, all technical terms used herein have the same meaning as commonly understood by one of ordinary skill in the art to which this invention belongs.

By the term "dose" is meant a predetermined aliquot of composition having a predetermined amount of active ingredient contained therein. Multiple doses may be administered to a patient at about the same time, with each unit being administered considered a separate dose.

As used herein, the phrase "feverfew extract" means a multi-component mixture obtained after subjecting feverfew plant material to a reagent (e.g., a solvent) that removes components of the feverfew plant material. Feverfew extracts may be in a dry, liquid or semi-solid form. One or more of a feverfew plant's parts, e.g., stem, leaf, root seed and flower, can be used to obtain a feverfew extract.

By the term "ginger extract" is meant means a multi-component mixture obtained after subjecting ginger plant material to a reagent (e.g., a solvent) that removes components of the ginger plant material. Ginger extracts may be in a dry, liquid or semi-solid form. One or more of a ginger plant's parts, e.g., stem, leaf, root seed and flower, can be used to obtain a ginger extract.

Although compositions and materials similar or equivalent to those described herein can be used in the practice or testing of the present invention, suitable methods and materials are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1 is a table showing the results of NF-κB p65 activity with Feverfew extract and/or LPS in monocyte cells.

FIG. 3 is a table showing results from an experiment in which LPS induced significant amounts of NO production and a combination of LPS and feverfew significantly inhibited nitrate and nitrite.

DETAILED DESCRIPTION

Figure 2:
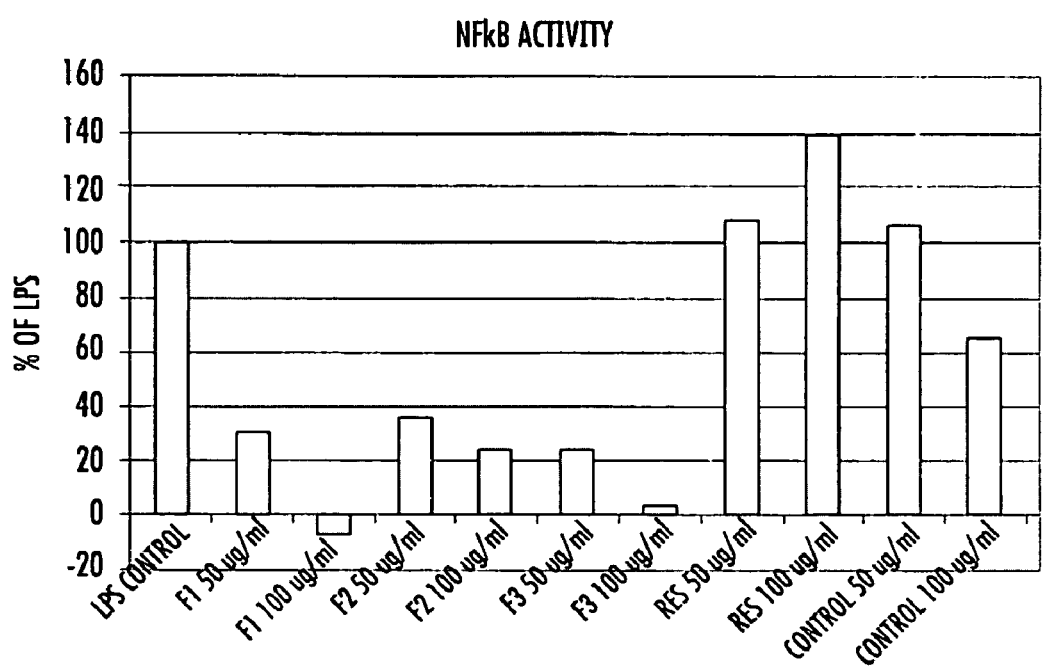
FIG. 2 is a graph showing the results of NF-κB p65 activity with Feverfew extract and/or LPS in monocyte cells.
Figure 4:
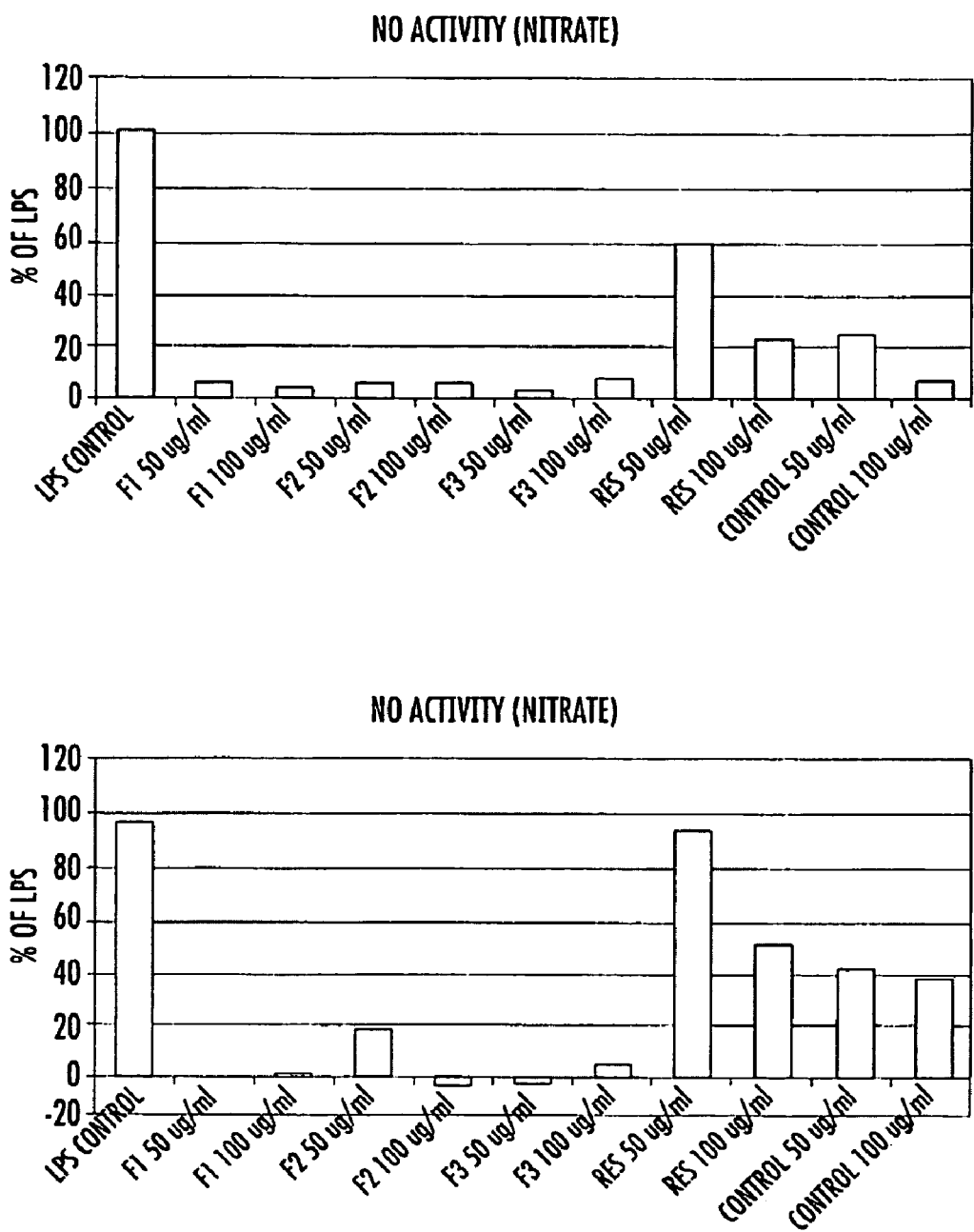
FIG. 4 is a pair of graphs showing results from an experiment in which LPS induced significant amounts of NO production and a combination of LPS and feverfew significantly inhibited nitrate and nitrite. Nitrous oxide expressed as nitrite activity as percent of LPS stimulation.

The invention encompasses compositions including feverfew extract, and in some embodiments, feverfew extract and ginger, for treating and preventing migrainous headaches and the symptoms associated with migrainous headaches. Methods of using feverfew and ginger are well known in the art, and are described, for example in PDR for Herbal Medicines, Thompson Medical Economics, Second Edition, Feverfew: 306, 309, and Ginger: 339, 342, 2000; Murphy, J J Lancet 1988 Jul. 23; 2(8604): 189-192; and Johnson, E S British Medical Journal 1985 Aug. 31; 291(6495):569-573. The below described preferred embodiments illustrate adaptations of these compositions and methods. Nonetheless, from the description of these embodiments, other aspects of the invention can be made and/or practiced based on the description provided below.

The administration of a very small amount of parthenolide, and more preferably feverfew, sublingually in a lipid-based composition as described below has been found to be an effective treatment for migraine headaches and their associated symptoms, including acute relief of migraine headaches and their associated symptoms as well as prevention of the onset of migraine headaches and their associated symptoms. Typically, each occurrence of a migrainous headache may be treated in a single dose. The treatment as described herein may be administered for the acute relief of a migrainous headache and its associated symptoms, from any time beginning with the first sign of impending migraine headache through such time as the migrainous headache is well underway. In some individuals, the first sign of an imminent migrainous headache may be other than the first mild pain, e.g., classic migraine aura, most often changes in visual perception which are unique, and which the sufferer has learned to associate with impending migraine. In others, the occurrence of unusual aches, pains, or changes in mood or irritability may signal that a migraine onset is imminent. Treatment of one of these symptoms may prevent the further development of the migraine headache.

The symptoms associated with migrainous headaches that are found to be relieved include nausea, vomiting, photophobia and phonophobia. The compositions and methods described herein have also been found to be effective in the treatment of headaches experienced by those not having been previously diagnosed with migraine, and whose headaches may not specifically qualify as migraine per the presently accepted diagnostic criteria of the International Headache Society, as well as in the treatment of headaches associated with excessive alcohol use.

The compositions and methods described herein may also be used daily as a prophylactic treatment, or as needed as a prophylactic treatment. For example, the individual can be administered a total administered amount of a composition in response to the occurrence of a predetermined event that the individual has identified as being associated with a higher incidence of migraine for them personally. Such events include menstruation, climate changes, air travel, etc. This prophylactic administration has been found to be effective in preventing or minimizing the onset and occurrence of migrainous headaches and their associated symptoms. The compositions and methods of the invention may also be used to treat headaches and symptoms (e.g., hangovers) associated with and resulting from the consumption of alcohol.

The compositions described herein are lipid-based, which results in the compositions having increased stability over non-lipid-based compositions (such as aqueous compositions). Additionally, use of lipids for forming the compositions is advantageous because lipids are compatible with the oil-soluble actives that are included in the compositions. Oil-soluble actives include but are not limited to: parthenolide, 3-beta-hydroxy-parthenolide, costunolid, reynosin, 8-beta-hydroxy-reynosin, tanaparthin-alpha-peroxide, canin, artecanin, secotanapartholide, 6-hydroxykaempferol 3,6-dimethyl ether, quercetagetin 3,6-dimethyl ether, quercetagetin 3,6,3'-trimethyl ether (accompanied by isomeric 3,6,4'-trimethyl ether), apigenin (also apigenin 7-glucuronide), luteolin (also luteolin 7-glucuronide), chrysoeriol, santin, jaceidin, and centaureidin. Any suitable lipids can be used for forming the compositions. In a typical embodiment, oil with a high oleic acid content (e.g., 70% or greater) is used as the source of lipids. Oleic acid acts as a vasodilator, and has been reported to be able to increase the permeation of lipophilic drugs through the skin and buccal mucosa by transcellular pathway. Examples of oils having high oleic acid contents are olive oil, canola oil, sunflower oil, soybean oil, palm oil, and macadamia nut oil. Olive oil is preferred in some embodiments due to the oleocanthal content in olive oil. Studies have revealed that, like ibuprofen, oleocanthal inhibits COX-1 and COX-2 enzyme activity. Because inhibition of COX activity underlies the anti-inflammatory actions of ibuprofen and other non-steroidal anti-inflammatory drugs (NSAIDs), these studies suggest oleocanthal is a natural anti-inflammatory agent.

The low concentrations of the active ingredients (e.g., feverfew and ginger extracts) of the compositions described herein obviates obtaining a prescription for use of the compositions as an effective treatment of migraine headaches. The ability to effectively treat migraine headaches and their associated symptoms using such low yet rapidly effective doses of active ingredient provides substantial benefits, including not only effective relief from migraine headaches and their associated symptoms, but also the drastic reduction in side effects which might otherwise be associated with said active ingredient. For example, the most commonly reported side effect of feverfew use is the occurrence of mouth sores, primarily associated with chewing feverfew leaves, which are observed in up to 11% of such users. Less frequently reported side effects of feverfew use include gastrointestinal side effects such as diarrhea, nausea, abdominal pain, indigestion, vomiting, and flatulence. Some users of feverfew have reported that when daily use is stopped suddenly after long periods of use, "post-feverfew syndrome" occurs (i.e., rebound headaches, anxiety, sleep disturbances, and muscle stiffness or pain) in about 10% of migraine patients who abruptly stop taking feverfew after a long history of daily use. Although most side effects are mild, it is nonetheless advantageous to avoid or mitigate their occurrence to the greatest extent possible while still employing an effective dose.

The methods and compositions of the present invention provide an improved safety profile, making the migrainous headache treatment more suitable to the average user, and ideally suited for those with whom additional caution need be exercised, e.g., those who are sensitive to various medications, pediatric use, where additional cautions are generally warranted, etc. The compositions and methods described herein are particularly beneficial to those patients concerned about using large amounts of medication for treatment of ailments, and also to patients who wish to avoid the use of prescription medications, or who cannot afford the use of prescription medications. Because nausea and vomiting are frequently associated symptoms of migraine, making it often unpleasant and sometimes difficult or even impossible to administer medications in solid form or by way of larger volumes of liquids, the low total administered amount of active ingredient and relatively small amount of total composition that is applied sublingually may be of particular benefit to those treating acute migraine. The compositions and methods provide migraine headache treatment to those wishing to employ migraine prophylaxis occasionally without the need to maintain daily intake of medication indefinitely. Additionally, the compositions and methods described herein provide a novel over-the-counter treatment for those suffering from migrainous headaches which may result in monetary savings associated with a decreased reliance on expensive prescription medications and the reduction in the economic burden of migraine in the US.

The compositions and methods of the invention for treating migrainous headaches provide a number of advantages over currently available migraine treatments. For example, currently available products are generally slow in providing relief while in contrast, the compositions and methods of the invention provide rapid relief of symptoms—typically within minutes of administration. While currently available treatments may be effective for some patients but not for others, the compositions and methods of the invention are effective for a large percentage of people who try this treatment, obviating a lengthy and sometimes costly search by an individual for the treatment that will be effective for that particular individual and thus reducing the time relief is felt.

A typical method of treating migrainous headaches and symptoms associated with migrainous headaches includes sublingually administering a lipid-based composition including parthenolide to a patient in need thereof in a total amount of from about 0.05 mg to about 1.0 mg of parthenolide in a two hour period. In another embodiment, a plurality of doses of parthenolide are sublingually administered over a 24 hour period, the total amount of parthenolide being about 0.05 mg. to about 1.0 mg. In this embodiment, the individual doses of parthenolide each do not exceed about 0.20 mg. Preferably, the parthenolide is administered in one to six doses in a 24 hour period.

Liquid compositions for treating migrainous headaches are provided, and can include parthenolide in an amount of from about 0.01 mg/ml to about 1.00 mg/ml, and more preferably from about 0.050 mg/ml to about 0.70 mg/ml. In another embodiment, the liquid composition includes feverfew extract in an amount of from about 1 mg/ml to about 10 mg/ml. As an example, migrainous headaches may be treated by administering a liquid composition including parthenolide sublingually to a patient in need thereof in a total administered amount of about 0.05 mg to about 1.0 mg of parthenolide in a two hour period. More preferably, the total administered amount is from about 0.050 mg to about 0.70 mg of parthenolide, and most preferably, the total administered amount is from about 0.08 mg to about 0.6 mg of parthenolide in a two hour period.

Because there is an increasing demand for natural ingredients in treatments for disorders, a particularly preferred embodiment of the present invention includes administration of small quantities of feverfew extract. For example, migraine headaches and/or their associated symptoms are treated by administering a lipid-based composition including feverfew sublingually to a patient in need thereof in a total administered amount of from about 3 mg to about 60 mg of feverfew extract in a two hour period. More preferably, the total administered amount is from about 3 mg to about 45 mg of feverfew extract, and most preferably the total administered amount is from about 3 mg to about 30 mg of feverfew extract in a two hour period. In another embodiment of the present invention, a plurality of doses of feverfew extract are administered sublingually over a 24 hour period, the total amount of feverfew extract not exceeding about 90 mg. Preferably, the individual doses of feverfew extract each does not exceed about 15 mg. In a preferred embodiment, the feverfew extract is administered in one to six doses in a 24 hour period.

Feverfew extract is derived from the feverfew plant Tanaecetum parthenium, which is known by a number of other names, including Chrisanthemum parthenium, Pyrethrum parthenii, Tanacete parthenii herba or folium, Chrysanthemum parthenium, Matricaria parthenoides, Leucanthemum parthenium, Matricaria parthenium, Spanish pellitory, Featherfew, Matricaria parthenium, Featherfoil, feather-fully, etc. Feverfew extract and ginger extract may be obtained by techniques known in the art using solvents such as petroleum spirits, polar organic solvents, and supercritical fluid extraction. See U.S. Pat. No. 5,384,121 to Rhodes, and also WO 94 06800; EP 0 553 658; WO 92 11857; GB 2,166, 952; EP 98 041; WO 98 39018. Additional extraction methods include: Organic Solvent Extraction, Maceration, Percolation, Countercurrent Extraction, Cold Pressing and Extraction with Supercritical Gases. Gases suitable for supercritical extraction include carbon dioxide, nitrogen, methane, ethane, ethylene, nitrous oxide, sulfur dioxide, propane, propylene, ammonia, and sulfur hexafluoride. An advantage of supercritical extraction is that it can take place at low temperature, thus preserving the quality of temperature-sensitive components.

Parthenolide is a sesquiterpene lactone that is present in large quantities in the extract of the feverfew plant. A feverfew extract can additionally contain other components such as Flavonoids including: 6-hydroxykaempferol 3,6-dimethyl ether, quercetagetin 3,6-dimethyl ether, quercetagetin 3,6,3'-trimethyl ether (accompanied by isomeric 3,6,4'-trimethyl ether), apigenin (also apigenin 7-glucuronide), luteolin (also luteolin 7-glucuronide), chrysoeriol, santin, jaceidin, and centaureidin; Polyynes; and Volatile oils including camphor, borneol and others, each of which may contribute to the therapeutic effect of the preparation disclosed herein. Feverfew is also known to contain several non-ubiquitous chemicals, including tenetin 3-b-hydroxyparthenolide, seco-tanaparthenolide A, 1-Beta-hydroxyarbusculin, 10-Epicanin, 8-Beta-reynosin, Apigenin-7-glucoside, Chrysanthemolide, Chrysanthemonin, Chrysartemin-A, Chrysartemin-B, Santamarin, Tanaparthin, Tanaparthin-1-alpha, 4-alpha-epoxide, Tanaparthin-1-beta,4-beta-epoxide, canin, artecanin, balchanin, Cosmosiin, L-Borneol, L-camphor, Mangoliolide, and Reynosin.

In some embodiments of the invention, compositions including the extract of feverfew are generally preferred for use in the present invention as compared to compositions including a highly purified parthenolide that has been isolated from the additional components naturally occurring in feverfew extract because feverfew extract may contain additional beneficial components. In a typical embodiment, compositions as described herein include feverfew extract that has been standardized to contain a predetermined standardized parthenolide concentration of preferably not less than about 0.7%, e.g., from about 1.0% to about 20%. Compositions including higher concentrations of parthenolide are encompassed by the invention, and may favorably reduce the amount of liquid required in the composition for delivery of the active to the user. Although the source of parthenolide is typically feverfew, parthenolide can also be obtained from any number of other plant species, where it generally occurs in substantially lower concentrations. Examples of such plant species include other members of the Compositae family, which include the many species of chrysanthemums, daisies, marigolds, chamomile, yarrow and aster. Another example of a plant from which parthenolide can be obtained is tansy. Compositions of the invention can alternatively include a synthetic form of parthenolide.

In some embodiments, compositions as described herein include additional active ingredients. Any suitable active ingredient that provides treatment of migrainous headaches or other physical benefits, and that does not adversely affect the treatment benefit of parthenolide and/or the feverfew extract can be used. For example, additional amounts of already present sesquiterpene lactones or additional sesquiterpene lactones can be incorporated in the compositions described herein. Particularly useful sesquiterpene lactones include those which are known to be contained in (naturally occur in) feverfew, such as balchanin, 3-Beta-hydroxyparthenolide, seco-tanaparthenolide A, santamarin canin, artecanin, chrysanthemonin, chrysartemin A and B, as well as those occurring in other plant species such as cinerenin, artemisinin, aristolactone, lactarorufin A, bilobalide, encelin, leucanthin B, enhydrin, melampodin A, tenulin, confertiflorin, burrodin, psilostachyin A, costunolide, guaianolide, helenalin, furandiol. Sesquiterpene lactones in addition to parthenolide may be isolated from plants such as dandelion, burdock, butterburr, mugwort and sunflower plants, among others. As another example, additional amounts of already present flavonoids or additional flavonoids can be incorporated in a composition described herein. Particularly useful flavonoids include 6-hydroxykaempferol 3,6-dimethyl ether, quercetagetin 3,6-dimethyl ether, quercetagetin 3,6,3'-trimethyl ether (accompanied by isomeric 3,6,4'-trimethyl ether), apigenin (also apigenin 7-glucuronide), luteolin (also luteolin 7-glucuronide), chrysoeriol, santin, jaceidin, and centaureidin.

Additional naturally occurring components and extracts can be included in compositions of the invention, e.g., those as identified in the HPUS. Such additional components include extracts indicated for use in treatment of nausea, inflammation, anxiety, or headaches. Particularly useful additional components are the extracts of ginger and/or green tea, or the isolated components thereof. L-theanine is a component isolated from green tea and may be preferred in some embodiments.

It has been shown that the use of only active ingredients that are extracted from herbs provides particular benefit to one suffering from migrainous headaches in being both effective in the treatment of a migrainous headache, and also providing natural healing conditions particularly suited to the well being of patients. Thus, a preferred composition of the invention contains substantially no active ingredients other than those that are extractable from herbal sources, and in a particularly preferred embodiment, a composition of the invention contains substantially no active ingredients other than those that are extractable from feverfew, ginger and green tea sources. In another preferred embodiment, the compositions contain substantially no active ingredients other than those that are extractable from feverfew and ginger. Such compositions can additionally include non-pharmacologically active ingredients, e.g., thickeners, carrier liquids and flavorants. As described herein, these natural ingredients have been found to be effective when administered in a sublingual regimen in the dosage ranges as described herein. The compositions of the invention typically contain parthenolide in the amounts as discussed earlier, and contain less than about 600 mg of any given natural active ingredient per dose.

The combination of feverfew extract and ginger extract is particularly effective in providing relief from migrainous headaches when provided and administered as taught herein. The combination of these extracts in the present compositions has been shown to provide synergistic effect in relieving both the pain and the nausea and/or general discomfort associated with migrainous headaches that exceeds a mere additive effect of these extracts. In a composition containing feverfew extract and ginger extract, ginger extract is typically present in a total administered amount not exceeding about 600 mg, preferably not exceeding about 375 mg of ginger extract in a two hour period. Particularly preferred compositions include ginger extract at a concentration of about 0.1% to about 10% (e.g., 0.1, 0.5, 1.0, 1.5, 2.0, 2.5, 3.0, 3.5, 4.0, 4.5, 5.0, 5.0, 6.0, 6.5, 7.0, 7.5, 8.0, 8.5, 9.0, 9.5, 10.0, 10.2%) of the total composition.

In another preferred embodiment, a liquid composition including feverfew and ginger extracts additionally includes L-theanine as an isolated component or as a constituent of green tea extract. In the composition, L-theanine is present in a total administered amount preferably not exceeding about 600 mg of L-theanine in a two hour period. Preferred compositions include L-theanine at a concentration of about 0.1-10% of the total composition.

A typical composition for treating migrainous headaches and symptoms associated therewith is in the form of a liquid. Generally, such a liquid composition is formulated using a carrier liquid appropriate for administration to the sublingual region of the mouth. To increase retention of the liquid composition sublingually for a time sufficient to allow absorption of the active ingredients in by the patient, a thickening agent can be included. Thickening agents are particularly useful in sublingual applications, because a more viscous agent is more easily retained in the appropriate area and further reduces the user's involuntary and premature impulse to swallow. A thickening agent, therefore, can improve the clinical efficacy of the composition by enhancing sublingual liquid retention for a time appropriate for proper absorption of the active ingredient by the patient. Thickening agents are well known in the art, and any suitable thickening agent may be used in the compositions of the invention.

The compositions described herein are provided in combination with a mucosal permeation enhancer in some embodiments. Any suitable mucosal permeation enhancer that enhances the mucosal absorption of the composition can be used. Examples of mucosal permeation enhancers include oleic acid, Azone, dimethylaminoacetate, chitosan, sodium lauryl sulfate, sodium deoxycholate, and cyclodextrins. Suitable adjuvants, such as preservatives, can additionally be included.

Compositions as described herein are typically administered sublingually, and can be administered sublingually using any appropriate technique, e.g., with a medicine dropper, syringe, vial, etc. The lipid-based composition is preferably administered in a controlled manner as a flow of liquid, rather than as a spray. A flowing liquid dispenser provides benefits of controlled delivery of the liquid to the desired position in the mouth, enhancing the likelihood that the composition to be dispensed is properly delivered. In a typical embodiment, the composition is administered using a unit dose applicator that is a dispenser having a reservoir and a delivery spout and having a liquid capacity, for example, of about 0.1 to about 10 mls. In a preferred embodiment, the unit dose applicator is provided as a dispenser having parthenolide in an amount not exceeding about 1.0 mg, or other limited quantities as discussed above. Alternatively, the unit dose applicator is provided as a dispenser having feverfew extract in an amount not exceeding about 50 mg, or other limited quantities as discussed above.

Any suitable dispenser can be used for administering the compositions described herein. In a typical embodiment, a dispenser for administering a single sublingual dose of the feverfew-containing composition for acute treatment of migraine is used. Such a dispenser may be made with a flexible bulb, ampule, bladder, or other hollow body for containing a liquid preparation that is to be administered sublingually. A tubular spout or stem may be fashioned to provide a conduit through which the liquid preparation may flow when the flexible hollow body is squeezed between the fingertips of the person administering the migraine treatment. The stem may be formed integrally with the hollow body and may be configured to taper toward the fluid outlet. The stem may be angled to facilitate positioning the outlet beneath the tongue when the medication is being administered. A break-away seal may be affixed to the outlet upon completion of the process of filling the dispenser. The seal may be made by heat welding the outlet or any other process. The dispenser may be made from any suitably flexible material such as polyethylene, polypropylene, nylon, foil, saran, or other polymer suitable for use with food and drug materials and which may be sealed after filling under sterile conditions or alternatively will withstand post-process sterilization.

An individual can administer a feverfew-containing composition for treatment of migraine by breaking the seal of the dispenser, positioning the outlet of the stem beneath the tongue of the patient, and then squeezing the hollow body or bulb between the fingers. Squeezing the bulb will cause the medication to flow through the outlet into the patient's sublingual region. A particularly preferred dispenser is a foil structure heat-sealed tube dispenser commercially available from Unette Corporation, Wharton N.J. Alternatively, the dispenser may be an ampule designed to mate with a plunger of a syringe to facilitate controlled delivery of the composition, such as described in U.S. Pat. No. 6,328,715.

In use of a composition of the present invention, a person in need of treatment administers the composition as described herein sublingually in an amount preferably not exceeding about 1.5 mg of parthenolide, or alternatively, not exceeding about 60 mg of feverfew extract. Typically, the composition is administered as a plurality of sublingual applications in order to maximize effective uptake of the active ingredient by the patient, for example, for those whose headache may require more composition than can be conveniently administered in one application for its effective or entire relief. Preferably, the composition is administered as a first sublingual application of a first composition including not exceeding about 0.75 mg of parthenolide, or alternatively, not exceeding about 30 mg of feverfew, which first composition is held in place under the tongue for a predetermined time, preferably about 60 seconds or more, after which the composition is swallowed. It is believed that 60 seconds provides an adequate amount of time for the actives from each pre-measured dose to be absorbed without producing a gag reflex. Most preferably, the composition is circulated or "swished" around the mouth by the patient prior to swallowing. The addition of this step to the procedure noticeably increases the effect of the composition in the treatment. A second composition not exceeding about 0.75 mg of parthenolide, or alternatively, not exceeding about 30 mg of feverfew, is then applied and held under the tongue for a predetermined time, preferably about 60 seconds or more, after which the second composition also is swallowed. Again, preferably the composition is circulated or "swished" around the mouth by the patient prior to swallowing. Alternatively, the total administered amount not exceeding about 1.5 mg of parthenolide, or alternatively about 60 mg of feverfew extract, may be divided among three or more compositions for sequential application as described above. This divided dosage administration technique of course may be utilized in the alternative modes of administration sublingually as described herein.

As an alternative to the unit dose applicator preferentially utilized as described above, a bottle designed so as to dispense only a certain, measured dose may be used. Alternatively, the composition may be provided in a conventional bottle with instructions to measure a dose, with or without a dedicated appliance for so doing (e.g. cup, syringe). Alternative delivery vessels that do not deliver premeasured quantities of liquid lack the advantages of convenience and higher probability of administration of the correct amount of the composition, but may be more economical than delivery of the composition using a unit dose system.

EXAMPLES

The present invention is further illustrated by the following specific examples. The examples are provided for illustration only and should not be construed as limiting the scope of the invention in any way.

Example 1

Effects of SF—$CO_2$ Feverfew Extract on NF-κB Activity and Nitric Oxide Production Scope of Study
This study was carried out to determine the bioactivity of proprietary super-critical fluid $CO_2$ (SCF—$CO_2$) extraction products from raw feverfew powder. An in vitro study was designed to test if these extracts have anti-inflammatory properties, by testing their ability to inhibit two well-defined biomarkers of inflammation: NFkB and NOS.

Study Products
The products used in this study were three (3) SCF—$CO_2$ extracts of feverfew, as well as the raw feverfew starting material (Unfractionated Control), and the residue left over from the extraction process (Residue).
The samples were labeled as follows:
Fraction 1 (F1): Pharmed 2-1; extracted at 200 atm pressure, 40° C.
Fraction 2 (F2): Pharmed 2-2; extracted at 300 atm pressure, 40° C.
Fraction 3 (F3): Pharmed 2-3; extracted at 600 atm pressure, 40° C.
Fraction C (Unfractionated Control): raw feverfew powder,
Fraction R (residue): feverfew residue (remaining after extraction)
Effect of feverfew fractions on NF-κB p65 activity
The transcription factor NF-κB is implicated in the regulation of several genes that code for mediators of the immune, acute phase and inflammatory responses. It can be activated by a number of stimuli including lipopolysaccharides (LPS). Treatment of cells with inducers results in the phosphorylation, ubiquitination and subsequent degradation of I-κB proteins. This results in the release of NF-κB dimers (p65/p50, p50/p50) into the nucleus where they activate appropriate target genes.

Materials and Methods

Cell line: Mouse monocyte cells (Raw 264.7) were grown in Dulbecco's Minimal Essential Medium (DMEM) supplemented with 10% fetal bovine serum (FBS) and antibiotics in a 5% $CO_2$ incubator.

Extraction of nuclear extract: $3\times10^6$ cells were cultured overnight in 5 ml of DMEM containing 0.5% FBS and antibiotics prior to drug treatment for starvation in 6-well plates. On the following day, culture fluids were replaced with fresh medium (0.5% FBS) and treated with 50 and 100 ug/ml of Feverfew fractions in duplicate and incubated in the $CO_2$ incubator for 2 h. Afterwards 20 ng/ml Lipopolysccaride (LPS—elicitor of NF-κB and pro-inflammatory cytokines) was added to one set of wells in order to compare with Feverfew fractions alone. The control treatments were Phosphate buffered saline (PBS-blank) and LPS alone. The plates were incubated for 4 more hours before preparation of nuclear extract. The cells were scrapped after washing with phosphatase inhibitors and nuclear extracts prepared from each group following nuclear extract protocol of the supplier, Active Motif, Calif. Protein estimation of the nuclear extracts was done following the Lowry's method in order to calculate the volume required for aliquoting equal amount of protein for NF-κB ac NF-κB p65 activity analysis: 2 μg protein was used for analysis of NF-κB activity assay (Active Motif, Calif.). The NF-κB chemiluminescent ELISA protocol was used for NF-κB p65 activity quantitation according to manufacturer's protocol. The relative light units (RLU) were converted into percentage NF-κB activity based on the activity in LPS (20 ng/ml)-treated sample.

Results

FIG. 1 and FIG. 2 show the results of NF-κB p65 activity with feverfew and/or LPS in monocyte cells. LPS-induced NF-κB p65 activity (100%) was significantly reduced by feverfew fractions 1, 2 and 3. The residue and unfractinated feverfew (control) did not have any visible inhibitory effect of LPS-induced expression. Both unfractionated feverfew and fraction 2 appeared to stimulate NF-kB activity in the absence of LPS. The data also suggest that Fraction 3 inhibits both the constitutive expression as well as the LPS induction of NFkB.

Effect of Feverfew Fractions on Nitric Oxide Production

Monitoring cellular NO production is a useful tool for determining nitric oxide synthase (NOS) activity. In the cell, NO undergoes a series of reactions with several molecules present in biological fluids and is eventually metabolized to nitrite ($NO_2$) and nitrate ($NO_3$). Since NO per se is volatile in nature, the best method of NO production is the sum of both nitrite and nitrate.

Materials and Methods

Mouse monocyte cell line was used for the assay. Cells were grown in nitrate free medium (MEM) for 24 before plating in multiwell plates. Cells ($0.5\times10^6$/ml) were plated in multiwell plates in 0.5% FBS-containing MEM medium overnight prior to the addition of feverfew. The wells were replaced with fresh medium on the next day and feverfew fractions (50 and 100 ug/ml) were added and incubated for 2 h. Later LPS (20 ng/ml) was added and kept for an additional 22 h. The medium was removed and analyzed for the nitric oxide using the Nitric oxide quantitation kit (Active Motif, Calif.). Both nitrate and nitrite concentrations (μM) were measured and plotted.

Results

LPS induced significant amounts of NO production (positive control). Feverfew fractions did not induce nitrate or nitrite molecules. Residue and control (whole feverfew) appeared to induce a low amount of endogenous nitrate. When feverfew was combined with LPS, there was significant inhibition of both nitrate and nitrite. Fractions 1 and 3 appear to be stronger inhibitors. Both residue and whole feverfew also reduced LPS-induced NO although their effects were inferior to fractions.

Extract fractions F1-F3 demonstrate inhibition of NF-κB with F3 exhibiting the greatest degree of inhibition while the residue and control samples demonstrate minimal enhancement of activity.

All samples demonstrated inhibition of NO production; however, the effect was far greater for fractions F1-F3 than residue or unfractionated feverfew.

The LPS-induced NFkB activity was significantly inhibited by the material in fractions #1, 2, & 3. Contrarily, the residue and unfractionated feverfew (control) showed no visible inhibitory effect and may in fact have minimal stimulatory effects. Fraction #1 tested at 100 ug/ml demonstrated inhibition of the LPS-induced NFkB activity by 46.7%.

For the NO-inhibition studies, all samples showed inhibition of LPS-induced NO production. It appears that the sample concentration was too high in the NO studies to show any dose-response effects. Further dilution of samples might differentiate between the fractions and demonstrate greater inhibitory differences between them. This may be revisited to perform dose-response test if the TNF-a assay is not suitable (see below)

Other Embodiments

Any improvement may be made in part or all of the components. All references, including publications, patent applications, and patents, cited herein are hereby incorporated by reference. In any listing of possible components, mixtures of possible components are contemplated unless expressly indicated otherwise. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of treating acute migrainous headaches, comprising:
   sublingually administering a non-aqueous, lipid-based composition in liquid form to a patient, the non-aqueous, lipid-based composition consisting essentially of:
   (1) a lipid having an oleic acid content of 70% or greater,
   (2) feverfew extract, and
   (3) ginger extract,
   wherein the non-aqueous, lipid-based composition has increased stability as compared with aqueous solutions, and delivery Of the non-aqueous, lipid-based composition in liquid form sublingually to a patient in need thereof provides rapid bodily absorption of the feverfew extract and the ginger extract to facilitate migraine relief,
   wherein the composition is delivered in one or more individual doses not exceeding about 30 mg of feverfew extract.

2. The method of claim 1, wherein the lipid is selected from the group consisting of: olive oil, canola oil, sunflower oil, soybean oil, palm oil, and macadamia nut oil, and combinations thereof.

3. The method of claim 1, wherein said the feverfew extract has a standardized parthenolide concentration of from about 0.70% to about 20%.

4. The method of claim 1, wherein the oleic acid content of 70% or greater acts as a mucosal permeation enhancer.

5. The method of claim 1, wherein said individual doses are administered sequentially.

6. The method of claim 1, wherein said composition is held sublingually for at least about 60 seconds prior to swallowing.

7. The method of claim 1, wherein said composition is circulated about the mouth prior to swallowing.

8. A method of acute treatment of migrainous headaches, comprising
   sublingually administering a non-aqueous, lipid-based composition in liquid form to allow rapid bodily absorption of the non-aqueous, lipid-based composition, the non-aqueous, lipid-based composition consisting essentially of
   (1) a lipid having an oleic acid content of 70% or greater,
   (2) feverfew extract and
   (3) ginger extract,
   wherein the non-aqueous, lipid-based composition has increased stability as compared with aqueous solutions, and delivery of the non-aqueous, lipid-based composition sublingually to a patient in need thereof in liquid form facilitates timely pain relief as compared to non-liquid, non-sublingual delivery methods,
   wherein the non-aqueous, lipid-based composition is delivered in two or more individual doses not exceeding about 30 mg of feverfew extract.

* * * * *